United States Patent
Opsal et al.

(10) Patent No.: US 7,613,598 B2
(45) Date of Patent: Nov. 3, 2009

(54) GLOBAL SHAPE DEFINITION METHOD FOR SCATTEROMETRY

(75) Inventors: Jon Opsal, Livermore, CA (US);
Hanyou Chu, San Jose, CA (US);
Xuelong Cao, Fremont, CA (US);
Youxian Wen, Livermore, CA (US)

(73) Assignee: KLA-Tencor Corp., Milpitas, CA (US)

( * ) Notice: Subject to any disclaimer, the term of this patent is extended or adjusted under 35 U.S.C. 154(b) by 624 days.

(21) Appl. No.: 11/542,806

(22) Filed: Oct. 4, 2006

(65) Prior Publication Data

US 2007/0040852 A1 Feb. 22, 2007

Related U.S. Application Data

(63) Continuation of application No. 10/784,619, filed on Feb. 23, 2004, now Pat. No. 7,145,664.

(60) Provisional application No. 60/463,791, filed on Apr. 18, 2003.

(51) Int. Cl.
*G06F 17/50* (2006.01)
(52) U.S. Cl. .................. 703/13; 702/40; 700/121; 382/151
(58) Field of Classification Search .............. 703/13, 703/14; 702/27, 40; 356/625; 700/121; 257/79; 382/151
See application file for complete search history.

(56) References Cited

U.S. PATENT DOCUMENTS

| 5,607,800 | A | 3/1997 | Ziger .................... 430/8 |
| 5,739,909 | A | 4/1998 | Blayo et al. ............ 356/369 |
| 5,867,276 | A | 2/1999 | McNeil et al. .......... 356/445 |
| 5,889,593 | A | 3/1999 | Bareket ................. 356/445 |
| 5,963,329 | A | 10/1999 | Conrad et al. ......... 356/372 |
| 6,278,519 | B1 | 8/2001 | Rosencwaig et al. ... 356/369 |
| 6,429,943 | B1 | 8/2002 | Opsal et al. ............ 356/625 |
| 6,483,580 | B1 | 11/2002 | Xu et al. ................ 356/300 |
| 6,704,661 | B1 * | 3/2004 | Opsal et al. ............. 702/27 |

(Continued)

FOREIGN PATENT DOCUMENTS

WO WO 01/97280 A2 12/2001

(Continued)

*Primary Examiner*—Paul L Rodriguez
*Assistant Examiner*—Kandasamy Thangavelu
(74) *Attorney, Agent, or Firm*—Morrison & Foerster LLP

(57) ABSTRACT

A method for modeling samples includes the use of control points to define lines profiles and other geometric shapes. Each control point used within a model influences a shape within the model. Typically, the control points are used in a connect-the-dots fashion where a set of dots defines the outline or profile of a shape. The layers within the sample are typically modeled independently of the shape defined using the control points. The overall result is to minimize the number of parameters used to model shapes while maintaining the accuracy of the resulting scatterometry models.

19 Claims, 17 Drawing Sheets

U.S. PATENT DOCUMENTS

| | | | |
|---|---|---|---|
| 6,778,911 B2 | 8/2004 | Opsal et al. ................... 702/27 |
| 6,919,964 B2 | 7/2005 | Chu ........................... 356/601 |
| 6,947,850 B2 | 9/2005 | Opsal et al. ................... 702/27 |
| 6,993,177 B1* | 1/2006 | Bachelder ................... 382/151 |
| 7,031,848 B2 | 4/2006 | Opsal et al. ................... 702/27 |
| 7,363,099 B2* | 4/2008 | Smith et al. ................. 700/121 |
| 2001/0051856 A1 | 12/2001 | Niu et al. ..................... 702/57 |
| 2002/0158193 A1 | 10/2002 | Sezginer et al. ............. 250/237 |
| 2003/0067496 A1* | 4/2003 | Tasker et al. ................ 345/846 |
| 2003/0147086 A1 | 8/2003 | Rosencwaig et al. ........ 356/601 |
| 2003/0151054 A1* | 8/2003 | Kuznicki et al. .............. 257/79 |
| 2003/0197872 A1* | 10/2003 | Littau et al. ................. 356/625 |
| 2004/0176928 A1 | 9/2004 | Johnson ....................... 702/182 |
| 2005/0231737 A1 | 10/2005 | Chu ........................... 356/636 |
| 2005/0280810 A1 | 12/2005 | Johnson ................... 356/237.5 |

FOREIGN PATENT DOCUMENTS

| | | |
|---|---|---|
| WO | WO 02/27288 A1 | 4/2002 |
| WO | WO 03/054475 A2 | 7/2003 |

\* cited by examiner

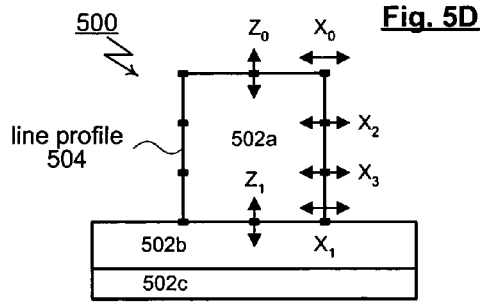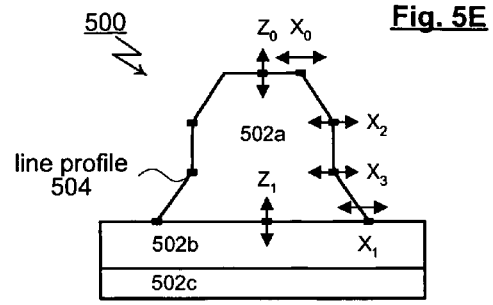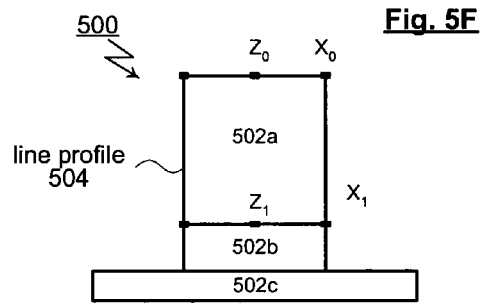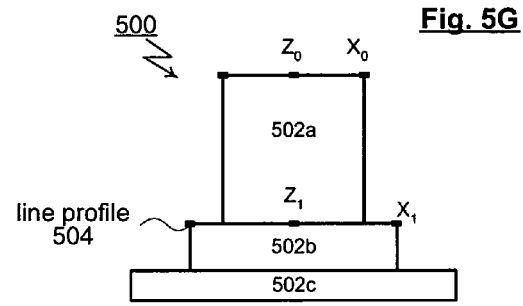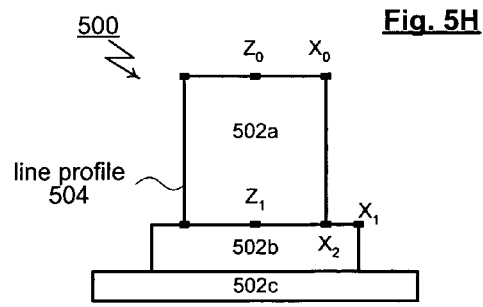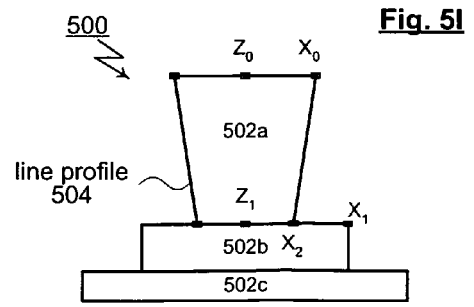

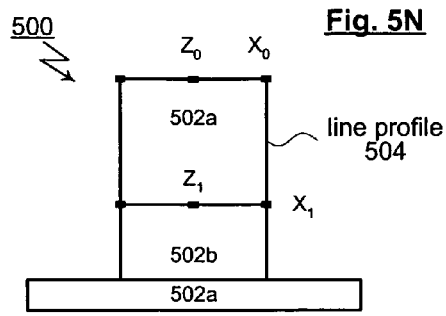
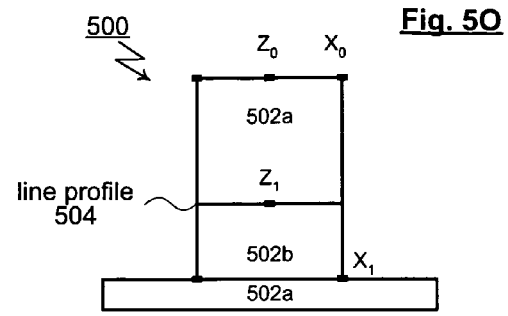
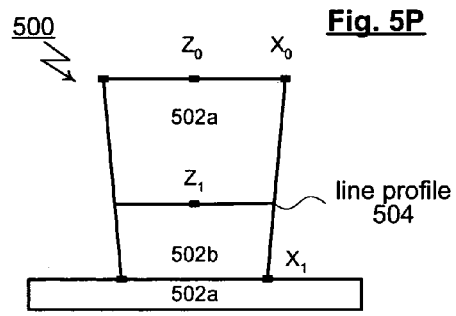
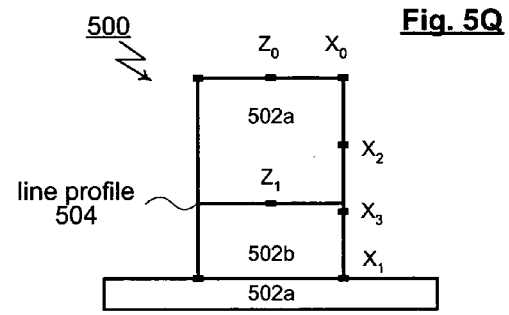
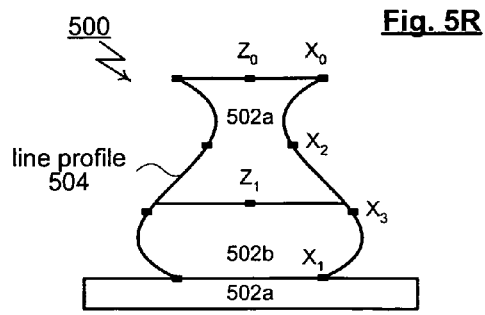

PR     Add a Width     Delete a Width

| Name: | Norm: | Min: | Max: | Fitting: | N Tries |
|---|---|---|---|---|---|
| PR Thickness: | 110.00000 | 0.000000 | 400.00000 | Yes ▼ | 0 |
| # of Slices | 1 | Snap to top: ☐ | | | |
| width | 45.610001 | 0.000000 | 500.00000 | Yes ▼ | 0 |

Global Parameters

| | From: | To: | Step: | Max Iterations: | Technology: |
|---|---|---|---|---|---|
| Wavelength range (nm): | 190 | 780 | 5 | 5 | SE+DC ▼ |
| | Norm: | Min: | Max: | Fitting: | |
| Pitch (nm): | 500.00000 | 100.0000 | 1000.0000 | No ▼ | Show More Paremeters |

More fitting params:

| | Norm: | Min: | Max: | Fitting: |
|---|---|---|---|---|
| Measurement angle: | 0.0000 | -10.0000 | 10.0000 | No ▼ |
| Mixing factor: | 0.0033 | 0.0000 | 1.0000 | Yes ▼ |
| Sidewall: | 0.0000 | 0.0000 | 1000.000 | No ▼ |
| Eccentricity: | 0.0000 | 0.0000 | 1.0000 | No ▼ |

More control params:

| | | | | |
|---|---|---|---|---|
| No Orders: | 9 | # of Thetas(BB): | 2 | |
| No Processors: | 1 | Interpolation: | Cubic-Spline ▼ | |
| Model Option: | FTM-Conical ▼ | Spline option: | 2 | |
| Fitting Option: | Levenberg-Marquar ▼ | Slicing option: | Adaptive ▼ | |
| # of Phis(SE): | 1 | Slice Scale: | 2 | |
| # of Thetas(SE): | 2 | Tolerance: | 2 | |
| # of Phis(BB): | 1 | | | |

606

| PR | | | | Add a Width | Delete a Width |
|---|---|---|---|---|---|
| Name: | Norm: | Min: | Max: | Fitting: | N Tries |
| PR Thickness: | 100.00000 | 0.000000 | 400.00000 | Yes ▼ | 0 |
| # of Slices | 1 | Snap to top: | ☐ | | |
| width | 45.610001 | 0.000000 | 500.00000 | Yes ▼ | 0 |
| width | 40.810001 | 0.000000 | 500.00000 | Yes ▼ | 0 |

610

604

610

602

US 7,613,598 B2

GLOBAL SHAPE DEFINITION METHOD FOR SCATTEROMETRY

PRIORITY CLAIM

This application is a continuation of U.S. patent application Ser. Nos. 10/784,619, filed Feb. 23, 2004 10/784,619, filed on Feb. 23, 2004, now allowed as U.S. Pat. No. 7,145,664 on Nov. 15, 2006, which in turn claims priority to U.S. Provisional Patent Application Ser. No. 60/463,791, filed Apr. 18, 2003, the disclosure of which is incorporated in this document by reference.

TECHNICAL FIELD

The subject invention relates generally to optical methods for inspecting and analyzing semiconductor wafers and other samples. In particular, the subject invention relates to methods for modeling samples for scatterometry and other applications.

BACKGROUND OF THE INVENTION

As semiconductor geometries continue to shrink, manufacturers have increasingly turned to optical techniques to perform non-destructive inspection and analysis of semiconductor wafers. Optical techniques typically apply an incident field (often referred to as a probe beam) to a sample and then detect and analyze the reflected energy. This type of inspection and analysis is known as optical metrology and is performed using a range of optical techniques. Scatterometry is a specific type of optical metrology that is used when the structural geometry of a sample creates diffraction (optical scattering) of the incoming probe beam. Scatterometry systems analyze diffraction to deduce details of the structures that cause the diffraction to occur.

Various optical techniques have been used to perform optical scatterometry. These include broadband spectroscopy (U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). In addition it may be possible to employ single-wavelength laser BPR or BPE to obtain critical dimension (CD) measurements on isolated lines or isolated vias and mesas. The above cited patents and patent applications, along with PCT Application No. WO03/009063, U.S. Publication No. 2002/0158193, U.S. Publication No. 2003/0147086, U.S. Publication No. 2001/0051856 A1, PCT Application No. WO 01/97280, U.S. Pat. No. 6,483,580, PCT Application No. WO 02/27288 and PCT Application No. WO 03/054475 are all incorporated herein by reference.

As shown in FIG. 1, a typical scatterometry system includes an illumination source that creates a mono or polychromatic probe beam. The probe beam is preferably focused by one or more optical components (lenses in this case) to create an illumination spot on the surface of the sample under test. A second series of optical components (lenses for this example) transports the diffracted probe beam to a detector. The detector captures the diffracted energy and produces corresponding output signals. A processor analyzes the signals generated by the detector using a database.

Scatterometry systems (like the one shown in FIG. 1) may be used to analyze a wide range of samples. A typical example, shown in FIG. 2, includes a scattering structure formed on a substrate. For this particular example, the scattering structure is a grating composed of a series of individual lines. In general, the scattering structure may be periodic (as in the case of FIG. 2) or isolated. Isolated structures include, for example individual lines or individual vias. The scattering structure of FIG. 2 is uniform (i.e., exhibits translational symmetry) along the Y axis. For this reason, the scattering structure is considered to be two-dimensional. Three dimensional scattering structures are also possible both in isolation (e.g., single via) or periodically (e.g., pattern of vias). The scatting structure is covered by an incident medium that is typically air but may be vacuum, gas, liquid, or solid (such as an overlaying layer or layers). One or more layers may be positioned between the scattering structure and the substrate. In most cases, the probe beam intersects the scattering structure at a normal angle (i.e., perpendicular to the lines that from the scattering structure). Conical scattering, where the probe beam intersects the scattering structure at a non-normal angle is also possible.

In most cases, a modeling process is used to translate the empirical measurements obtained during scatterometry into physical measurements such as line widths. For this process, a software model is used to represent the expected structure and composition of the sample. The software model is parameterized, allowing characteristics such as line widths and line profiles to be changed. Maxwell's equations are used to predict the diffraction that the modeled structure would impart to the probe beam of the scatterometer. A set of these predicted measurements are generated using variations to the parameters of the model. This process is repeated until the predicted measurements match the empirical measurements to a desired goodness of fit. At that point, the modeled structure and its associated parameters are assumed to match the sample.

To be accurate, the model used during the modeling process must reflect the structure and composition of the sample. For the example of FIG. 2, this can be relatively straightforward. The lines of the scattering structure in that example are rectangular in cross-section, allowing each line to be modeled using a small number of parameters (typically, line height and line width). Each line is further simplified by being composed of a single material and being geometrically invariant along the Y-axis. In practice, this relative simplicity is not always typical of samples. FIG. 3 shows, for example a sample that includes lines having rounded edges and sloping sidewalls. Adding additional complexity, the lines in the scattering structure of FIG. 3 are composed of multiple layers, each of which may have different dielectric properties.

Complex samples, such as the sample shown in FIG. 3 require correspondingly complex modeling techniques. For one of these techniques, a Riemannian approach is used to model geometric shapes (such as the lines) as stacks of slabs. For example, the line profile of FIG. 4A may be modeled using the stack of slabs shown in FIG. 4B. The height and width of each slab is chosen so that the stack of slabs approximates the shape being modeled. Portions of the shape that change rapidly (such as the foot or top of the line profile of FIG. 4A) can be accurately modeled by increasing the number of slabs while decreasing their thickness (not shown). Shape portions that are relatively constant may be modeled using fewer, thicker slabs. Models constructed using this technique require two parameters for each slab (height, width) or a total of 2N parameters for N slab models.

The slab-based technique necessarily introduces a degree of roughness into the resulting model. This roughness gives the model edges a staircase-like appearance attributable to the rectangular cross-section of the individual slabs. This side-effect can be reduced by using slabs that have a trapezoidal cross-sections or quadrilateral cross-sections. The use of trapezoid slabs is shown in FIG. 4C. The overall effect is a reduction in stair-stepping at the cost of additional parameters. For trapezoidal cross-sections, three parameters are required for each slab (height, width and one interior angle). Quadrilateral cross-sections require four parameters (height, width and two interior angles).

Quadrilaterals or trapezoids are an effective method for increasing the accuracy of the modeling process. At the same time, the increased number of parameters adds further complexity to an already arduous computational process. As a result, there are continuing efforts to find modeling methods that provide high accuracy while limiting the number of required parameters. This is the goal of the method described, for example in U.S. Pat. No. 5,963,329 (incorporated in this document by reference). For this method, the familiar slab-based approach is used to model lines and other geometric shapes. In this case, however, the slabs are subdivided into one or more sub-profiles. Each sub-profile has a reference edge and a reference height. The width of each slab in a sub-profile is defined using an offset (which may be positive or negative) from the reference edge. The height of each slab in a sub-profile is defined as a multiple of the reference height. Each sub-profile also has two scaling factors, one for height and a second for width. Changing the height scaling factor increases or decreases the height of all of the slabs in a sub-profile making the sub-profile taller or shorter. Changing the width scaling factor spreads the sub-profile—slabs that are narrower than the reference edge become narrower still, slabs that are wider than the reference edge become even wider. By controlling the scaling factors for each sub-profile, the overall profile of the line can be varied to produce a range of differing shapes.

The use of sub-profiles and associated scaling factors decreases the number of parameters that are required to define a particular shape. Unfortunately, the use of rectangular slabs suffers from the staircase limitations already described. It is also true that the use of scaling factors is only beneficial when computational results can be re-used as the scaling factors are changed. For cases where this is not possible, the use of scaling factors is computationally similar to more traditional methods for defining slab heights and widths.

For these reasons and others, a need exists for scatterometry techniques that avoid the limitations of traditional modeling methods. This need is particularly apparent for high density semiconductor wafers where feature sizes are small.

SUMMARY OF THE INVENTION

The present invention provides a global shape definition method for modeling samples. For this method, a control-point based approach is used to define the geometric shapes within samples. As an example, consider the case of a sample that includes one or more lines. The profile (i.e., the cross-sectional outline) of a representative line is defined using a set of control points. Each control point influences the shape of the line profile. For some cases, this means that control points define shapes in a connect-the-dots fashion. For other cases, a more complex mathematical function, such as Bezier or Spline curve fitting, is used to translate a set of control points into a corresponding shape. It should be noted that the control points are preferably only used to define shapes. Layers within a shape can be modeled independently.

The present invention also provides an interactive environment for building and evaluating scatterometry models based on the global shape definition method. The interactive environment allows a user to specify multilayer scatterometry models. The user can add shape profiles by adding groups of control points. Once a model has been defined, the interactive environment may be used to calculate its optical response. The user may then compare the calculated optical response with an empirically generated optical response to visually assess goodness of fit. By modifying control points (by moving, adding or deleting) and changing layer properties, the user may interactively arrive at an accurate model for the sample.

BRIEF DESCRIPTION OF THE DRAWINGS

FIG. 9 is a diagram showing the layer property component of the visual design environment of FIG. 6.

FIG. 10 is a diagram showing the global parameters component of the visual design environment of FIG. 6.

FIG. 11 is a diagram showing the additional parameters component of the visual design environment of FIG. 6.

DETAILED DESCRIPTION OF THE PREFERRED EMBODIMENTS

Figure 1:
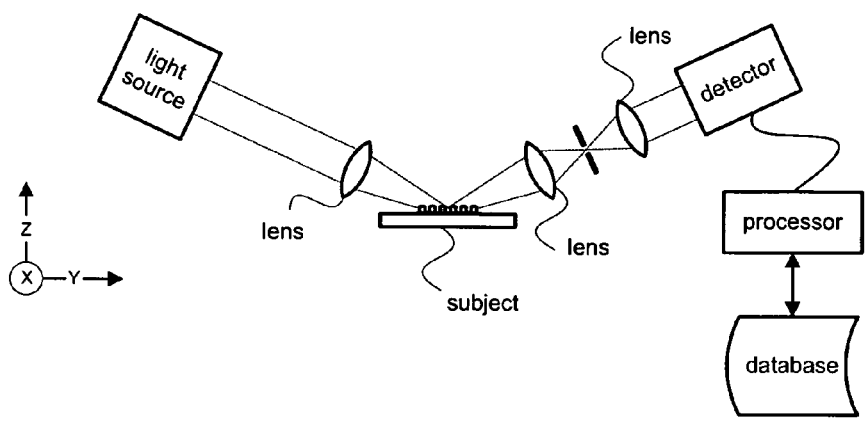
FIG. 1 shows a prior art optical metrology system.
Figure 2:
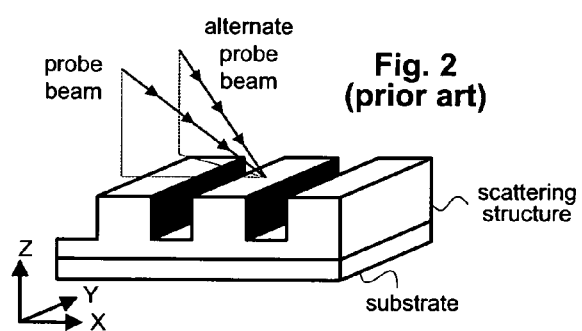
FIG. 2 is a diagram of an idealized prior art sample.
Figure 3:
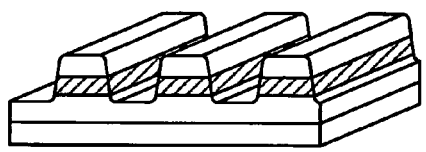
FIG. 3 is a diagram of a second idealized prior art sample.
Figure 4A:
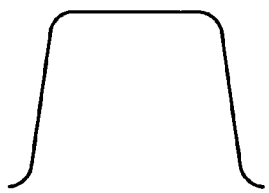
FIG. 4A is a diagram showing the line profile used in the sample of FIG. 3.
Figure 4B:
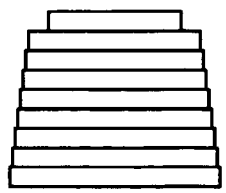
FIG. 4B is a diagram showing a model for the line profile of FIG. 4A where the model is constructed using a prior art slab-based technique.
Figure 4C:
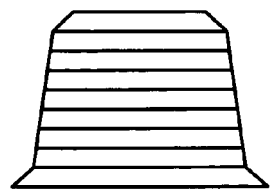
FIG. 4C is a diagram showing a model for the line profile of FIG. 4A where the model is constructed using a prior art trapezoidal technique.

The present invention provides a global shape definition method for modeling samples. For typical applications, the sample to be modeled is a semiconductor wafer of the type generally shown in FIGS. 2 and 3 and includes a scattering structure formed on one or more underlying layers. The lowermost of the underlying layers is commonly referred to as a substrate. The scatting structure is covered by an incident medium that is typically air but may be vacuum, gas, liquid, or solid (such as an overlaying layer or layers). In the most typical case, the scattering structure is a grating consisting of a periodic series of lines. By appropriate generalizations, other isolated or periodic features may also be modeled.

Figure 5A:
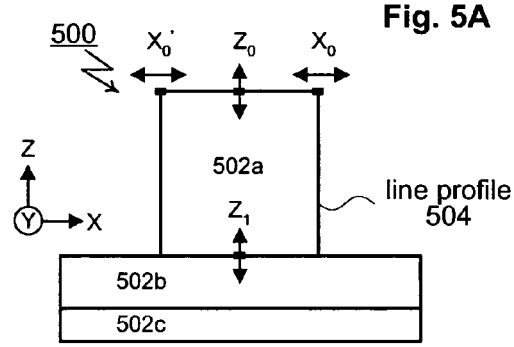
FIG. 5A through 5X show various samples modeled using a shape definition method as provided by an embodiment of the present invention.

For the global shape definition method, a control-point based approach is used to define the profiles (i.e., the cross-sectional outlines) of geometric shapes within the sample. FIG. 5A shows a sample 500 modeled using this approach. For this particular example, sample 500 includes three layers: an upper layer 502a, an intermediate layer 502b and a substrate 502c. Each of these layers will typically (but not necessarily) be formed using a different material type.

Sample 500 also includes a line profile 504. Line profile 504 has a height (i.e., Z dimension) and a width (i.e., X dimension) and is assumed to be invariant in the Y direction. In this example, line profile 504 includes only upper layer 502a. As will be described in more detail, this is representative and line profile 504 may include any number of layers. Line profile 504 is considered to repeat at periodic intervals in the +X and −X directions. As will be discussed later, the present invention includes controls that allow the nature of this repetition to be defined.

At a minimum two control points ($Z_0$ and $X_0$) are used to control the shape of line profile 504. The specific location of each control point may be varied to produce a range of different shapes. However, the location of each fundamental control point is also constrained according to the following rules:

$$Z_0(x_0, z_0)\ x_0 = 0$$

$$z_0 \geqq 0$$

$$X_0(x_0, z_0)\ x_0 \geqq 0$$

$$z_0 = h$$

where h is the height of line profile 504. In other words, $Z_0$ is free to move in the Z direction and $X_0$ is free to move in the X direction (as long as their respective Z and X values do not take on negative values). Thus, for this example, $Z_0$ defines line height and $X_0$ defines line width. In general, for the modeling method, each layer included in a line profile has at least two control points—one for height, and one or more for width. Each layer not included in a line profile has a single control point for height. Control points that define height are designated using the letter Z while those defining width are designated using the letter X.

Figure 5B:
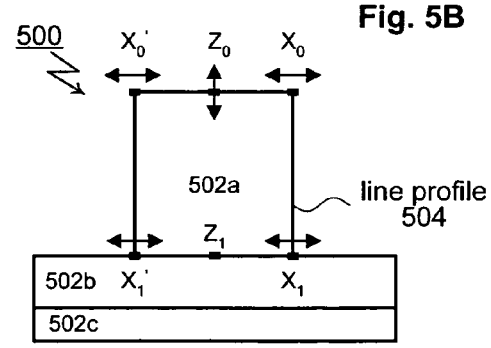

To increase the complexity of line profile 504, additional control points may be added. As shown in FIG. 5B, the first additional control point ($X_1$) is added at the base of line profile 504. Like control point $X_0$, control point $X_1$ can only moved in the X direction. Its Z coordinate is fixed:

$$X_1(x_1, z_1)\ x_1 \geqq 0$$

$$z_1 = 0$$

Figure 5C:
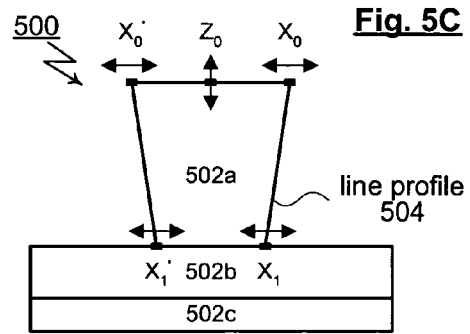

FIG. 5C shows the resulting changes to sample 500 when the position of $X_1$ is moved to narrow the base of line profile 504. At this point, it should be clear that the control points actually define half of line profile 504. Changes to the location of any control point is mirrored onto the opposite side of line profile 504. This explains why moving control point $X_1$ narrows the based of line profile 504 on both sides—not just the side where control point $X_1$ is located. In general, this use of symmetry is useful because it allows the number of control points to be minimized. Alternately, separate width varying control points may be used. This is especially useful when asymmetric line profiles are modeled.

FIG. 5D shows sample 500 after two more control points have been added to line profile 504. The new control points ($X_2$ and $X_3$) are spaced evenly along the right edge of line profile 504. Each controls width and not height. FIG. 5E shows the effect of moving control points ($X_0$ and $X_1$) while leaving the new control points ($X_2$ and $X_3$) fixed. As shown, line profile 504 is now narrowed at the top and widened at the base. Control points ($X_2$ and $X_3$) ensure that an intermediate portion between the top and base of line profile 504 remains vertical.

FIG. 5F shows an example where intermediate layer 502b has been added to line profile 504. Line profile 504 now has four control points (as mentioned previously, each layer in a line profile includes a control point for height and at least one control point for width). In this case, control points $Z_0$ and $X_0$ control the height and width of the portion of upper layer 502a that is included in line profile 504. Control points $Z_1$ and $X_1$ control the height and width of the portion of intermediate layer 502b that is included in line profile 504. FIG. 5G continues this particular example by showing the result of moving the $X_1$ control point. As may be appreciated, the portions of line profile 504 that corresponds to intermediate layer 502b is now wider than the portion that corresponds to upper layer 502a. FIGS. 5H and 5I show the result of adding (and then moving) an additional control point $X_2$. In this case $X_2$ has been added to the base of the portion of line profile 504 that corresponds to upper layer 502a. Movement of $X_2$ has narrowed that the base of that portion creating a sloping sidewall analogous to the example shown in FIGS. 5B and 5C.

Spacers

Figure 5J:
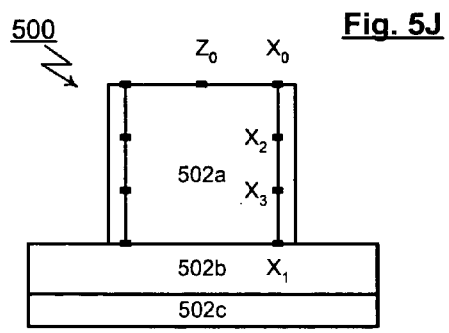
Figure 5K:
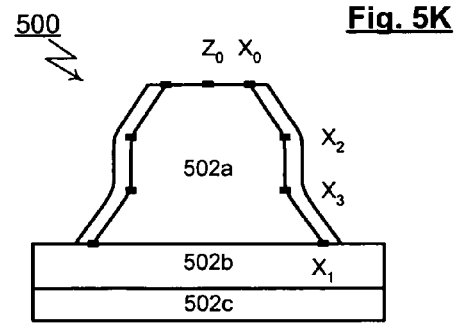

As shown in FIG. 5J, the modeling method may also be used to define layers that cover the sidewall of line profile 504. This type of structure, known as a "spacer" is unusual in the sense that it resembles a type of coating more than a traditional layer. The modeling method allows each line profile to have one or more associated spacers. Each is defined by its thickness and material type. Once defined, spacers follow the shape of the underlying line profile 504. This is shown, for example, in FIG. 5K.

Trench Fills

Figure 5L:
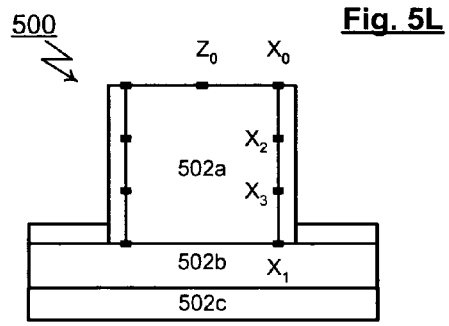
Figure 5M:
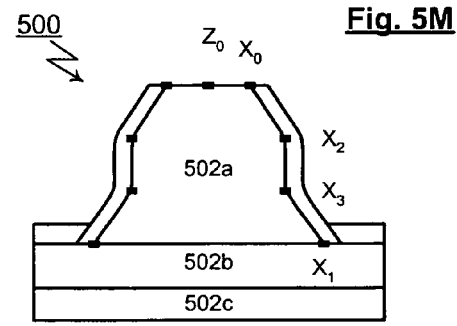

Trench fills are another type of structure that can be added using the modeling method. One or more trench fills may be added to each model, each specified by its thickness and material type. FIG. 5L shows a model 500 that includes a single trench fill as well as a spacer. FIG. 5M shows the same model after movement of two control points.

Global Shape Definition Option

In each of the preceding examples, control points are allocated on a per-layer basis. Each layer included in a line profile has a single control point that defines its height. Each layer also has one or more control points that define its width. Where more than one width defining control points is used, the result is typically a sidewall whose width varies in some way as a function of height (see examples 5C, 5E and 5I). It should be noted that the position of the width defining control points in one layer has no bearing on the size or shape of adjacent layers. The influence of control points is strictly local to the layers in which they are included. As an alternative, the modeling method may be configured to use global shape definition. To describe the global shape definition option, FIGS. 5N and 5O show two instances of a sample 500. In 5N, the previously described non-global method is used. FIG. 5O shows a similar sample constructed using the global shape definition option. In both Figures, line profile 504 includes two layers (upper layer 502a and intermediate layer 502b). In FIG. 5N (constructed with the local option) upper layer 502a includes control points $Z_0$, $X_0$, while lower layer 502b includes control points $Z_1$ and $X_1$. In FIG. 5O (constructed with the local option) the height varying control points ($Z_0$ and $Z_1$) are unchanged. The two width varying control points ($X_0$ and $X_1$) have been replaced by a single control point $X_0$ that controls the width of both layers. FIG. 5P shows the globally represented sample 500 after a movement of control point $X_0$. As may be appreciated, movement of the single control point has altered all portions of line profile 508 and is not limited to any layer 502.

FIG. 5Q continues this example by showing a globally constructed sample 500 that includes two layers 502 within the line profile 508. A total of four control points ($X_0$, $X_1$, $X_2$ and $X_3$) define the sidewall of line profile 508. It should be noted that the control points ($X_0$, $X_1$, $X_2$ and $X_3$) are spaced uniformly along line profile 508. Their positions are independent of the layers 502a and 502b included in line profile 508. FIG. 5R shows the same sample after the movement of control points $X_2$ and $X_3$. The result is a deformation of the sidewall of line profile 508 that is unrelated to the included layers 502a and 502b.

Upper layer 502a has a total of five control points ($Z_0$, $X_0$, $X_1$, $X_2$ and $X_3$). Intermediate layer 502b has two control points ($Z_1$ and $X_4$). In FIG. 5N, the control points $X_0$, $X_1$, $X_2$ and $X_3$ are evenly distributed over the sidewall of upper layer 502a. This follows because they directly control the shape of the portion of line profile 504 that corresponds to upper layer 502a. In FIG. 5O, the control points $X_0$, $X_1$, $X_2$ and $X_3$ are evenly distributed over the sidewall of both upper layer 502a and intermediate layer 502b. This follows because they control the entire sidewall of line profile 504.

The global option is notable, not just because the effect is different, but also because global shape definition effectively decouples profile definition from layer properties. When the global option is used, each layer requires only a single control point to define layer height. The remaining control points are shared between layers. Depending on the layers used and the profile shape, this can result in a further reduction in control points.

Local Distortion Option

Figure 5S:
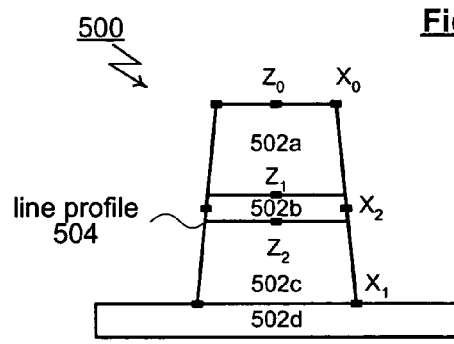

When the global shape definition option is active, each control point contributes to the overall shape of the line profile. To add flexibility, the modeling method allows local distortions to be added to create localized perturbations. To illustrate, FIG. 5S shows a model of a sample 500 that includes a local distortion. Sample 500 includes a total of four layers: an upper layer 502a, two intermediate layers 502b and 502c and a substrate 502d. Each of the non-substrate layers is included within the line profile of sample 500. The shape of that profile is controlled by width-varying control points $X_0$ and $X_1$ and height varying control points $Z_0$, $Z_1$ and $Z_2$.

Intermediate layer 502b is configured to include a local distortion. The same layer is also configured to "snap to top." This ensures that the uppermost point in the sidewall of intermediate layer 502b has the same width as the lowermost point in the sidewall of upper layer 502a. In other words, a smooth transition is enforced between layers 502a and 502b. The smooth transition means that there is no need for a control point at the top of intermediate layer 502b (typically, all layers include a control point at that position (see preceding examples)). As a result, the control point $X_2$ for intermediate layer 502b is relocated to a point intermediate between the top and bottom of intermediate layer 502b.

Figure 5T:
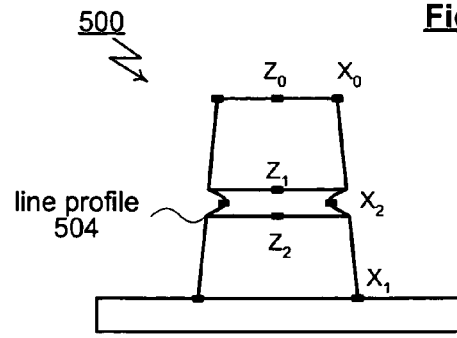

FIG. 5T shows the effect of moving the control point $X_2$. The result is a distortion that is limited to the portion of line profile 504 that is included within the top and bottom of intermediate layer 502b. Subsequent movements of other control points will change the global shape of line profile 504 but the local distortion will be maintained.

Modeling Non-Uniformities for Line Tops

Figure 5U:
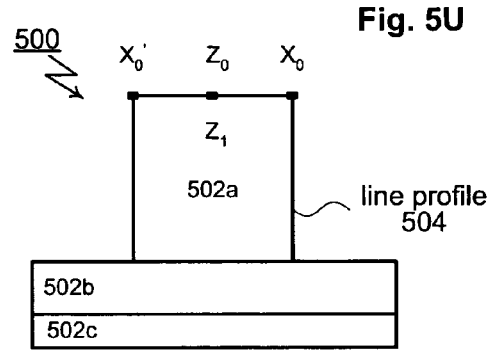
Figure 5V:
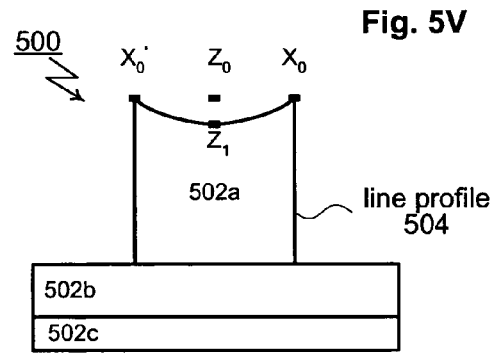

For the models described above, each layer has at most one height varying control point Z. To support more complex models, it is useful (in some cases) to add additional height varying control points within a single layer. As an example, consider the line profile 508 shown in FIG. 5U. In this case, line profile 508 has the width varying control point $X_0$ along with height varying control point $Z_0$ originally described for FIG. 5A. Line profile 508 also has an additional height varying control point $Z_1$ not included in the example of FIG. 5A. The additional height varying control point $Z_1$ is (at the time of initial definition) coincident with control point $Z_0$. As shown in FIG. 5V, moving the control point $Z_1$ has the effect of creating a depression in the top line profile 508. The overall height of line profile 508 is still controlled by control point $Z_0$. This is a simple example of a line profile that can not be modeling using the previously described single height varying control point per layer.

Figure 5W:
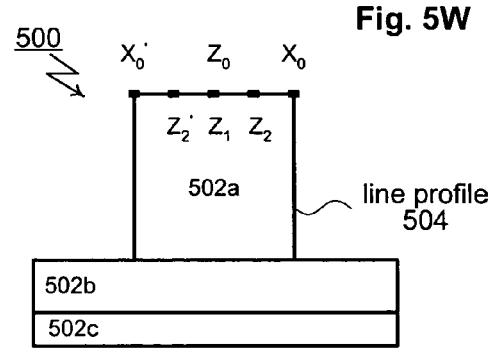
Figure 5X:
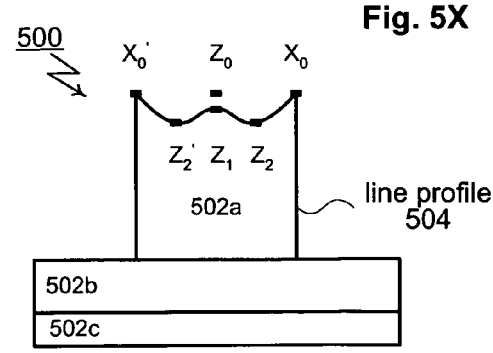

A more complex example is present in FIGS. 5W and 5X. As shown in FIG. 5W, two additional height varying control points ($Z_1$ and $Z_2$) have been added to the line profile 508 originally show in FIG. 5A. After a hypothetical movement of the additional control points, the line profile 508 of FIG. 5X is obtained. Once again, the overall height of line profile 508 is still controlled by control point $Z_0$.

The use of additional height varying control points provides a simple mechanism for extending the flexible sidewall modeling techniques to line tops. Using this technique, line tops may be arbitrarily shaped to represent a range of empirically encountered line profiles.

Spline Implementation

In general, it should be noted that a wide range of techniques may be used to translate the position of control points into corresponding curves. Of these, the simplest is to connect individual control points using straight line segments (i.e., a connect-the-dots approach). For the purposes of the present invention, it is more useful to use an approach that allows control points to describe arbitrary curves. Bezier and Spline functions are two examples of techniques of this type. For the specific implementation being described, a shape preserving B-spline curve is used to form the line profile 504. In cases where a small number of control points are used (e.g., FIGS. 5A, 5B and 5C) the result is that the individual control points are connected by straight lines (or at least appear to be connected by straight lines). For more complex structures, where more control points are used (e.g., FIGS. 5M and 5R) the individual control points appear to be connected by curves. With additional control points, it is possible to model shapes of arbitrary complexity.

Interactive Design Environment

The present invention (in at least some implementations) includes an interactive design environment for modeling semiconductors and other samples. Fundamentally, this is an environment that allows the types of models just described to be visually defined and evaluated. The following sections describe the components that combine to form the interactive design environment as well as their relationships to each other.

Figure 6:
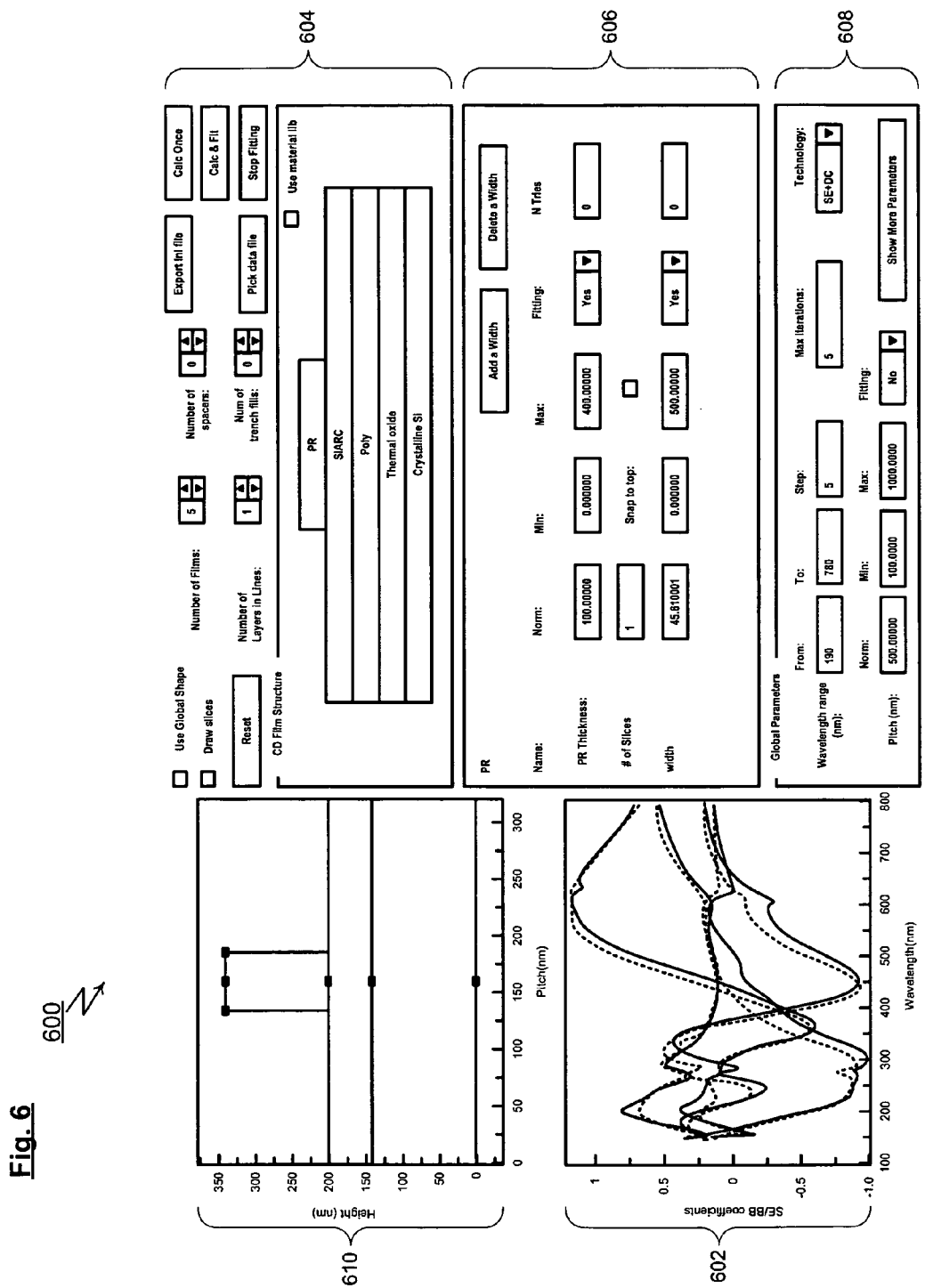
FIG. 6 is a diagram showing the visual design environment as provided by an embodiment of the present invention.
Figure 7:
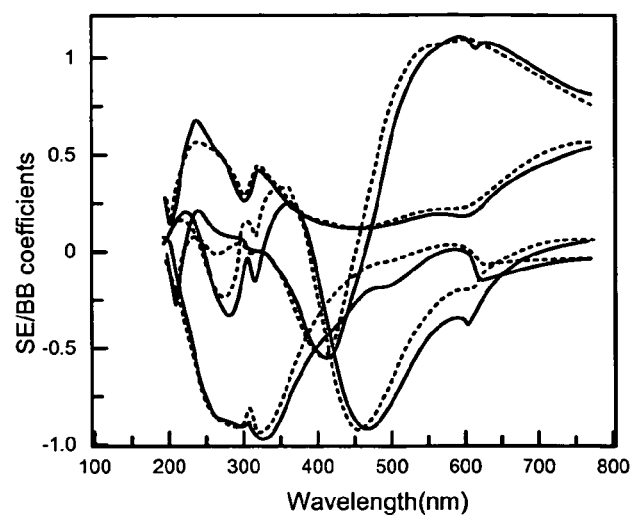
FIG. 7 is a diagram showing the spectral display component of the visual design environment of FIG. 6.

FIG. 6 shows the main interface 600 for the visual design environment. Main interface 600 includes a spectral fitting component 602, a film structure component 604, a layer property component 606, a global parameters component 608, and an interactive shape modeling component 610. As shown more clearly in FIG. 7, spectral fitting component 602 compares the theoretically generated response from the model (such as the models described in FIG. 5A through 5Q) to empirically obtained measurements. In this sense, spectral fitting component 602 is the end result of the visual design environment providing the user with important feedback of the success or failure of the design process.

Figure 8:
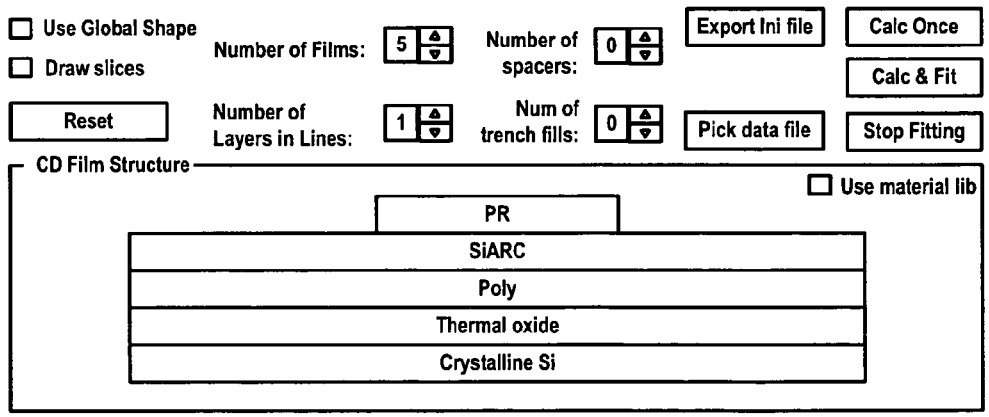
FIG. 8 is a diagram showing the film structure component of the visual design environment of FIG. 6.

As shown in FIG. 8, film structure component 604 includes a gross model definition. The gross model definition is a block like depiction of the layers that are currently included in the sample being modeled. For the particular example of FIG. 8, a five layer model is represented. This includes an upper layer (formed in photo-resist or PR), three intermediate layers (formed in SiARC, Poly and Thermal Oxide, respectively) and a substrate (formed in Crystalline Silicon).

A "Number of Films" control allows the user to increase or decrease the number of layers included in the gross model definition. Increasing the number of layers causes the upper layer to be replicated. In this case, that would result in an extra photo-resist layer being added to the top of the gross model definition. The type of material in each layer is interactively changeable (typically using a mouse activated popup menu). This allows the user to add layers, and then select the type of material used in the new layers. Decreasing the number of layers deletes the uppermost layer.

A "Number of Spacers" control allows the user to increase or decrease the number of spacers included in the gross model definition. Each spacer is created using a default material (typically replicating the material in the lowermost layer included in the line structure). The user may then interactively select an appropriate material as necessary (typically using a mouse activated popup menu).

A "Number of Trench Fills" control allows the user to increase or decrease the number of trench fills that are included in the gross model definition. Each trench fill is created using a default material (typically replicating the material in the lowermost layer included in the line structure). The user may then interactively select an appropriate material as necessary (typically using a mouse activated popup menu).

For the particular example of FIG. 8, only the PR layer is included in the line profile of the sample being modeled. Visually, film structure component 604 distinguishes layers included in the line profile by making them appear as narrow rectangles sitting on top of the wider rectangles used to represent layers not included in the line profile. This gives the gross model definition a rough line profile that allows the user to quickly deduce which layers are actually used to form the lines on the surface of a model. A "Number of Layers in Lines" control allows the user to increase or decrease the number of layers of this kind. In the case of FIG. 8, incrementing the value of the control would cause the SiARC layer to be included in the line profile for the sample being modeled. Decreasing the number would remove the PR layer from the line profile, leaving in this case, a model with no lines.

Film structure component 604 also includes a series of buttons to control calculation. This includes a "Calc Once" button, a "Calc & Fit" button and a "Stop Fitting" button. The "Calc Once" causes the visual design environment to evaluate the current model and display the resulting spectra using the spectral fitting component 602. The "Calc & Fit" button causes the visual design environment to initiate a regression-based analysis to minimize the differences between the spectra created by evaluating the current model and empirically obtained spectra. The regression-based analysis iteratively changes model parameters to reduce the difference between evaluated and empirical results. As discussed below, the visual design environment allows the user to specify the parameters to be changed along with appropriate step sizes and other details. The "Stop Fitting" button halts the regression process and displays the results of the last complete evaluation using the spectral fitting component 602.

Film structure component 604 includes a "Use Global Shape" option to enable or disable global definition (global shape definition is described above). An "Export Ini file" allows the user to specify and write a file containing a description of the current model. This allows the current model to be saved and reloaded for later analysis. A "Reset" button undoes any modification made to the model, resetting it to an initial state. Typically, that state is defined as the initial model state as loaded from a file. A "Pick Data File" button allows the user to specify and load a file containing empirical measurements for the sample being modeled.

As shown in FIG. 9, layer property component 606 includes a series of fields that describe a particular layer in the model being evaluated. For the specific example of FIG. 9, the layer property component corresponds to the PR layer. This can be changed by selecting (typically by a mouse click) one of the other layers in the gross model definition within film structure component 604. The fields included in layer property component 606 allow the user to specify the height of the corresponding layer using maximum, minimum and normal values. The user can also indicate whether variations in height should be used during regression analysis of the model. For the case where regression of this parameter is specified, the user can specify the number of steps to be used.

In a similar fashion, the fields included in layer property component 606 allow the user to specify the width of a layer using maximum, minimum and normal values. The user can also indicate whether variations in width should be used during regression analysis of the model. For the case where regression of this parameter is specified, the user can specify the number of steps to be used.

The "Add a Width" button allow the user to add additional control points to a layer. As an example, consider FIGS. 5A and 5B. The difference in these two figures is the additional control point $X_1$ in FIG. 5B. In the visual design environment, this can be accomplished by selecting upper layer 502a in the gross model definition and then activating the "Add a Width" button in the layer property component 606. Each added layer is given the same fields shown for existing layers allowing the user to select maximum, minimum and normal widths as well as regression options. The "Delete a Width" button allows the user to remove control points from a layer.

Layer property component 606 also allows the user to specify the number of slices that will be used to evaluate each layer. Slicing is discussed in more detail below.

As shown in FIG. 10, global parameters component 608 includes a series of fields that are global to the model being evaluated (i.e., not specifically related to any particular layer or structure). These include fields allowing the user to specify the range of wavelengths used during regression ("From", "To" and "Step"). In the example shown in FIG. 10, "Step" is set to five. This means that beginning from the 190 nm wavelength every $5^{th}$ measured data point is used for the regression analysis. The choice of the wavelength range is typically based on the usefulness of the data in terms of its information content, which for example may be influenced by the penetration depth of the incident light. Throughput considerations and the calculation speed also influence the choice of the wavelength discrimination The "Max iterations" option controls the number of iterations the regression algorithm should run. It is an integer value greater than zero. Higher numbers of iterations cause a longer computation time not necessarily yielding the global residual minimum. The choice of the iteration number must be made based on throughput considerations as well as the regression convergence performance after each sequence of the recipe. An iteration number between three and five is used for majority of the CD optical models.

includes SE+DC (spectral ellipsometry with DC component), SE−DC (spectral ellipsometry without DC component), BB (broadband), SE+DC+BB (spectral ellipsometry with DC component and broadband) and SE−DC+BB (spectral ellipsometry with broadband and without DC component). Additional information describing these parameters is found in U.S. Pat. No. 6,278,519. The disclosure of that patent is included in this document by reference.

Global parameters component 608 also includes a "Show More Params" button. Activating this button invokes the additional parameters component shown in FIG. 11. The additional parameters component includes the following fields:

| Field | Description |
|---|---|
| "Measurement angle" | This parameter represents the azimuth angle, which is the deviation from the ideal ninety degree angle between the SE incident beam and the orientation of the grating lines. |
| "Mixing factor" | Fitting this parameter enables compensation for contributions made by the surrounding material. |
| "Side wall" | enables spacer considerations such as a coating native oxide layer on a silicon trench line. |
| "Eccentricity" | this parameter is related to BB spot anomaly correction. |
| "No. orders" | number of Fourier reconstruction orders. This number is material dependent. For example, for dielectric films "No. orders" may be nine or lower, whereas for semiconducting films the number might approach twenty or higher. The line spacing ratio can also influence the number of orders. Number of orders and calculation time are proportional. |
| "No. processors" | for systems that support multiple processors, this integer parameter can be chosen to be greater than one. Single processors systems require "No. processors" equal to one. |
| "Fitting option" | In addition to the more commonly exploited Levenberg-Marquard regression search engine, Simple Box, Simulated Annealing, Principal Axis and the DE Generic Algorithms may be selected. |
| "# of Phis (SE)" | An integer (>0) that represents # of azimuthal angles used in numerical integration for SE. |
| "# of Thetas (SE)" | An integer ($\geq 0$) that represents # of incident angles used in integration for SE. # of Thetas = 0 activates the adaptive integration mode. |
| "# of Phis (BB)" | An integer in the range [0 10]. This parameter is related to the number of azimuthal angles used in integration for BB and is useful while using the conical model only. |
| "# of Thetas (BB)" | An integer in the range [−5, 10] which represents the number of incident angles used in integration for BB. |
| "Interpolation" | Cubic-spline is an example of one type of interpolation mode. |
| "Tolerance" | This option can be used together with the number of tries feature. It often results in significant timesavings during seed value determinations. The tolerance defines a lower residual limit for interruption of the calculations. In other words, the regression search terminates as soon as the residual value reaches the tolerance limit. Small tolerance values tend to increase the accuracy but also trade off with the calculation speed. |
| "Number of Tries" | This feature is often used during the initial sequence to determine correct seed values. The software divides the range into a number of sub intervals to more efficiently search for the optimum solution. The feature is time consuming, and once appropriate nominal values are determined, it is disabled in the final recipe. The Tolerance feature can be employed to achieve a faster nominal value search. |
| "Number of Slices" | This parameter identifies number of slices used for the sublayer. Assigning a negative sign to this number yields a smooth transition at the interface between the sublayer and the layer on top. It is realized by coupling the topmost shape control point of the sublayer to the lowest shape control point of the upper layer. The negative sign convention does not need to be used when the global shape option is employed. |

Another set of fields allows the user to specify the pitch (or line spacing) for the sample being modeled. These options take the form of normal, minimum and maximum values. The user can also specify whether line pitch is to be varied during regression. A final option allows the user to specify the type of measurement technology that will be used. Currently, this list As shown in FIG. 11, the additional parameters component also includes a "Model option" parameter. This allows the user to select the underlying algorithm that will be used to perform model evaluations. The following algorithms may be specified:

| | |
|---|---|
| "FTM-Simple" | layer-based RCWA Fourier expansion in the x-direction coupled with mode matching (matrix diagonalization) for vertical direction. FTM stands for Fast Transfer Matrix. |
| "FTM-Conical" | RCWA Fourier expansion in the x-direction coupled with mode matching for vertical direction. This algorithm is an improved RCWA approach using the so-called TM1 implementation. The model can handle overlays. |
| "G0-QMR" | (Quasi Minimal Residual Iterative Linear Solver): the model is a Green's function volume integral approach. It has proved to be a fast approach for low contrast materials. |
| "G1-QMR" | similar to the G0-QMR model. The Green's function is based on rectangular grating profiles. The model might be efficient for characterization of profiles that deviate little from straight ones. |
| "G-Born" | first order perturbation, simpler version of G1-QMR. |
| "GA-QMR" | generalized version of the G0-QMR model. |
| "FD-CON" | finite difference (vertical direction) conical version of the FD-CD model. |
| "FD-CD model" | non-conical finite difference model. It represents the fastest non-conical code. The model usually requires more slices than FTM-Simple model. It can switch to FTM-Simple for rectangular profiles. |

The additional parameters component also includes a "Spline option" parameter. This parameter allows the user to control the way in which control points are spaced. The following values are supported:

| | |
|---|---|
| 0 | Causes control points to be equally spaced. |
| [1, 10] | Causes control points to be more densely allocated near the boundaries with sigmoid-1. |
| [10, ∞) | Causes control points to be more densely allocated near the boundaries with sigmoid-2. |
| [−10, −1] | Causes control points to be more densely allocated at the top with sigmoid-2. |
| (−∞, −10) | Causes control points to be more densely allocated on the bottom with sigmoid-2. |

Figure 12A:
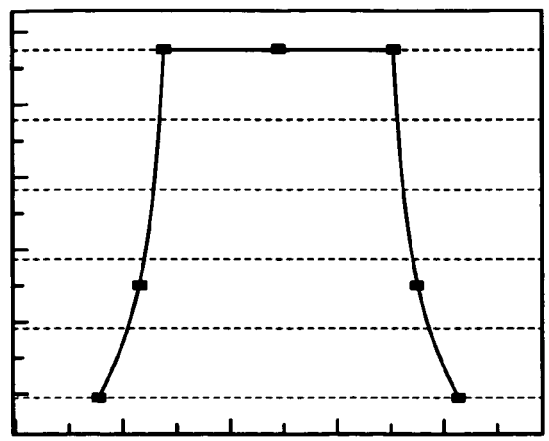
FIGS. 12A though 12C show equally spaced, adaptive and sigmoid methods for model slicing as provided by an embodiment of the present invention.
Figure 12B:
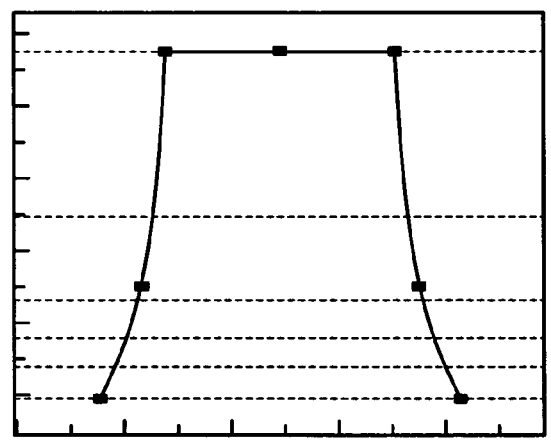
Figure 12C:
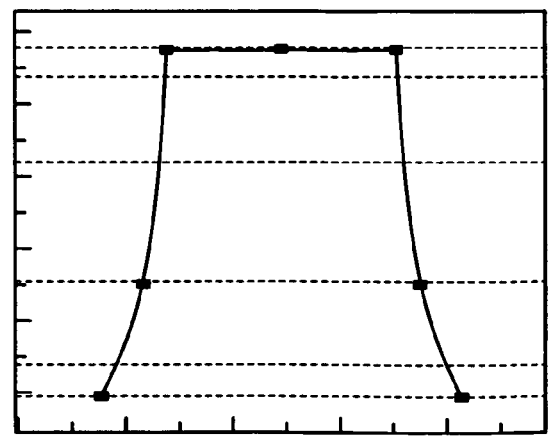

The additional parameters component also includes a "Slicing option" parameter. This allows the user to specify the scheme that will be used to slice the model for evaluation. As shown in FIG. 12A, the default slicing strategy divides the model into a series of equally sized slabs. Adaptive slicing, shown in FIG. 12B optimizes slicing placement to reflect the geometry being modeled. In particular, adaptive slicing places more slices near material boundaries (i.e., at layer tops and bottoms). Adaptive slicing also places more slices where sidewall geometry is complex or rapidly changing. Sigmoid slicing, shown in FIG. 12C is a type of adaptive slicing that uses a sigmoid function to vary slice density to optimize layer interfaces and sidewall geometry.

The additional parameters component also includes a "Slice scale" parameter. Slice scale provides a second mechanism for controlling the way layers within a model are sliced for evaluation. The following ranges are defined for slice scale:

| | |
|---|---|
| $s \leq 0.5$ | Number of slices ($n_s$) is controlled by the number of slices parameter. |
| $s > 0.5$ and slicing option set to "equally spaced" or "sigmoid." | $n_s$ is defined as $\frac{1}{2}|\varepsilon|kt$ (where $k = 2\pi/\lambda$, $t$ = height, and $\varepsilon$ is the permittivity). |
| $s > 0.5$ and slicing option set to "adaptive." | $\left|\frac{dw}{dh}\right||\varepsilon|kt$ |

Figure 13:
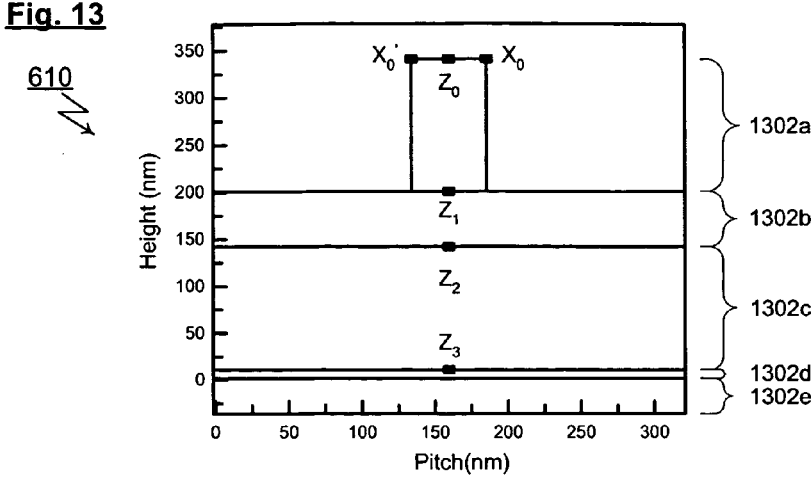
FIG. 13 is a diagram showing the interactive shape modeling component of the visual design environment of FIG. 6.

As shown in FIG. 13, interactive shape modeling component 610 includes a visual representation of the sample being modeled. For this particular example, interactive shape modeling component 610 displays five layers: an upper layer 1302, intermediate layers 1302b through 1302d and a substrate 1302e. These correspond to the PR, SiARC, Poly, Thermal Oxide, and Crystalline Silicon layers described for the gross model definition of film structure component 604. In the visual design environment, the heights of the non-substrate layers 1302a through 1302d are defined by the position of respective control points $Z_0$ through $Z_3$. The width of upper layer 1302a (and all layers included within the line profile) is defined by the control points $X_0$ and $X_0'$. The location of each control point is interactively movable, typically using a mouse or other pointing device. This allows the user to interactively change parameters such as layer thickness, line height and line width.

Figure 14A:
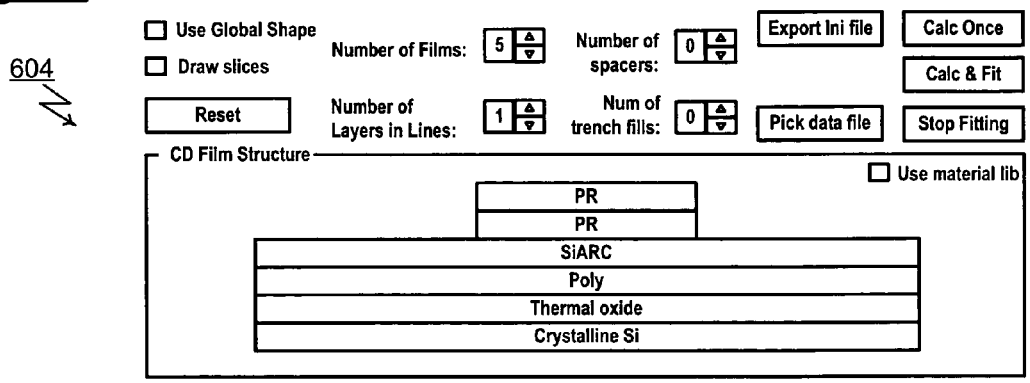
FIGS. 14A and 14B show the film structure component and the layer property component during development of a hypothetical model.
Figure 14B:
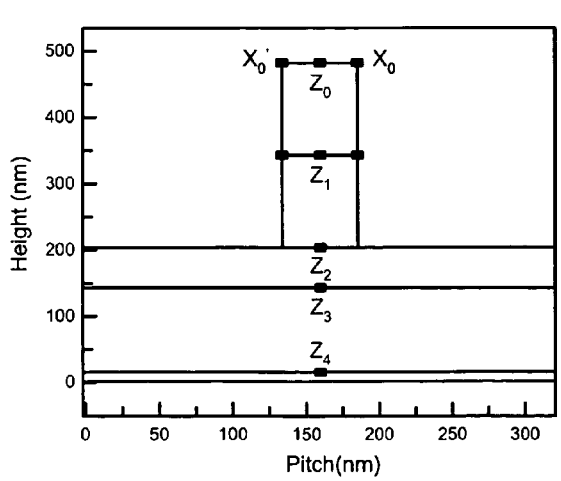
Figures 15A, 15B:
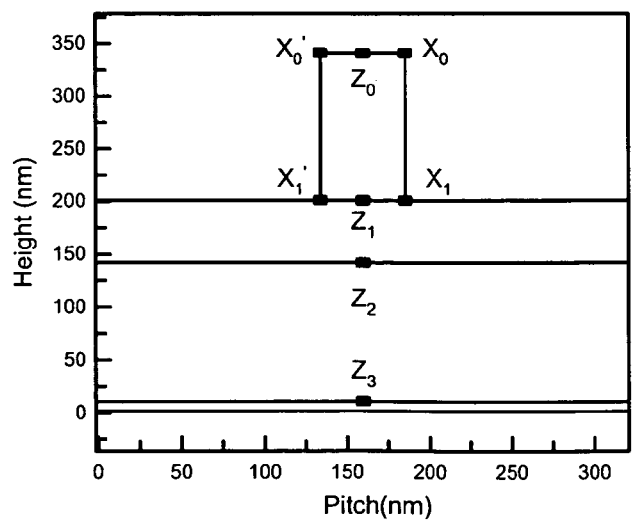
FIGS. 15A though 15C show the interactive shape modeling component and the layer property component during development of a hypothetical model.
Figure 15C:
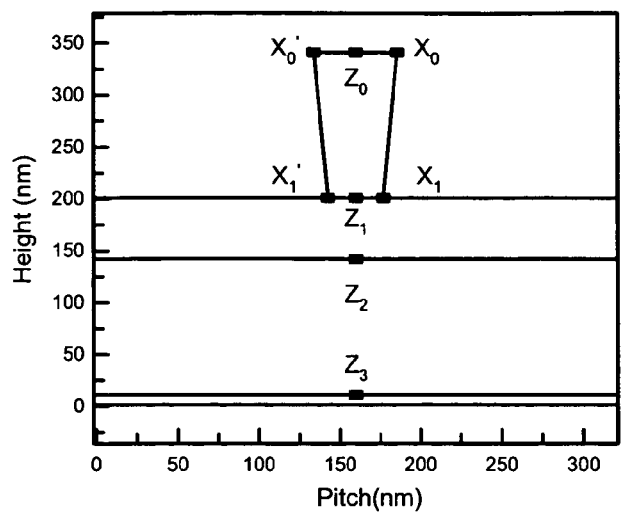

Interactive shape modeling component 610 works in concert with spectral fitting component 602, film structure component 604, layer property component 606, and global parameters component 608. Changes made in any single component are reflected across the remaining components. As an example FIG. 14A shows film structure component 604 after the "Number of Films" control has been increased from five to six. Within film structure component 604, this adds an additional layer to the gross model definition. As shown in FIG. 14B, this change is propagated to interactive shape modeling component 610 which now includes an additional layer and control point. As a second example, FIG. 15A shows layer property component 606 after activation of the "Add a Width" button. Within layer property component 606, this adds an additional width with maximum, minimum, normal values as well as a regression option. As shown in FIG. 15B, this change is propagated to interactive shape modeling component 610 which now includes an additional control point $X_1$. Interactively moving the control point $X_1$ as shown in FIG. 15C, results in a corresponding change in the size of the second width of the layer property component 606 shown in FIG. 15D.

Figure 16A:
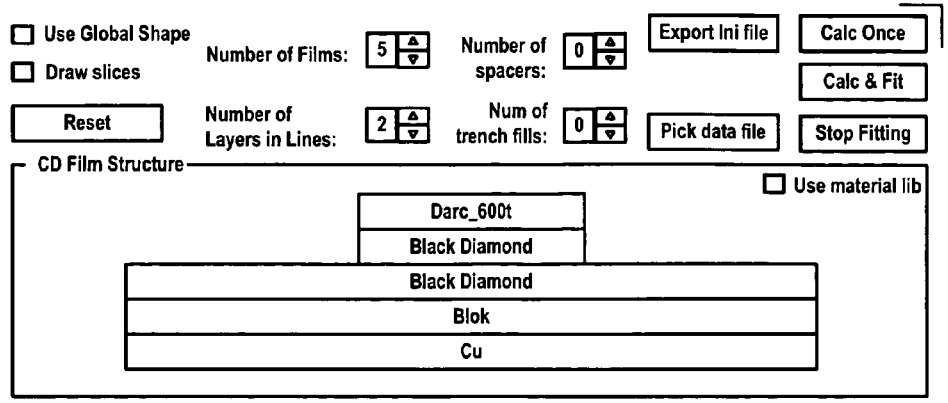
FIGS. 16A though 16E show various components of the visual design environment during development of a hypothetical model.
Figure 16B:
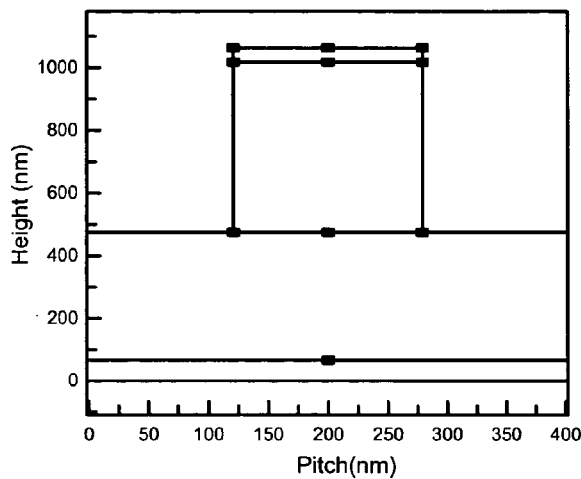
Figure 16C:
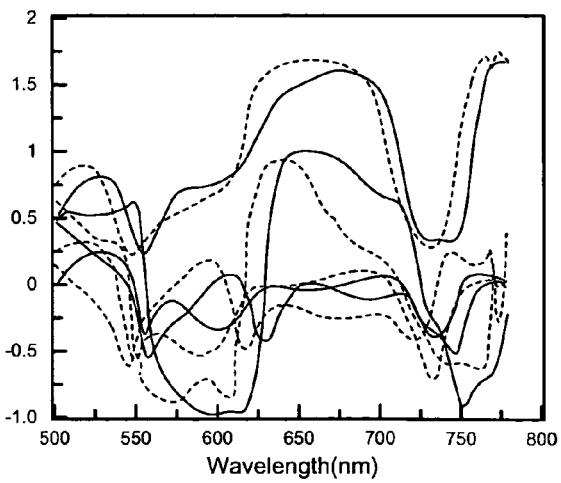
Figure 16D:
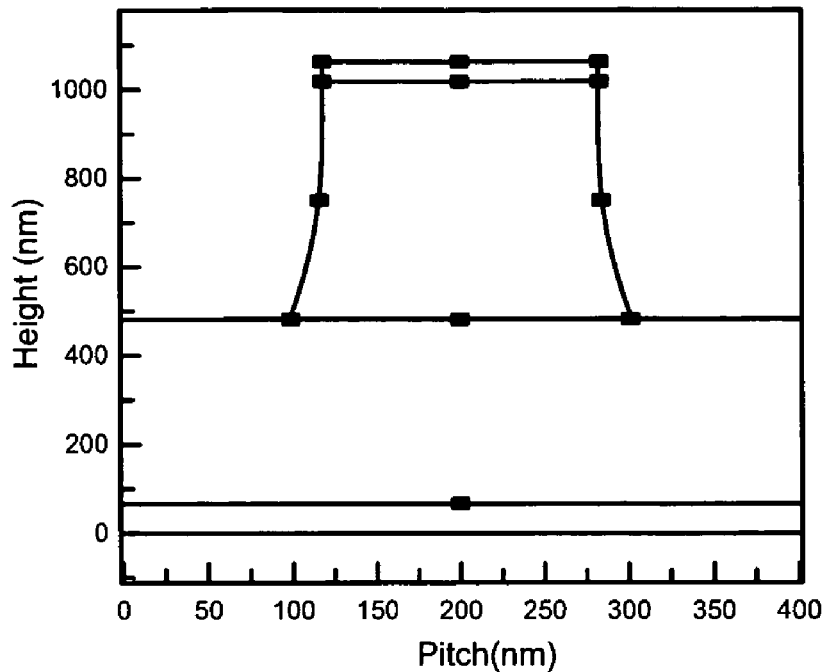
Figure 16E:
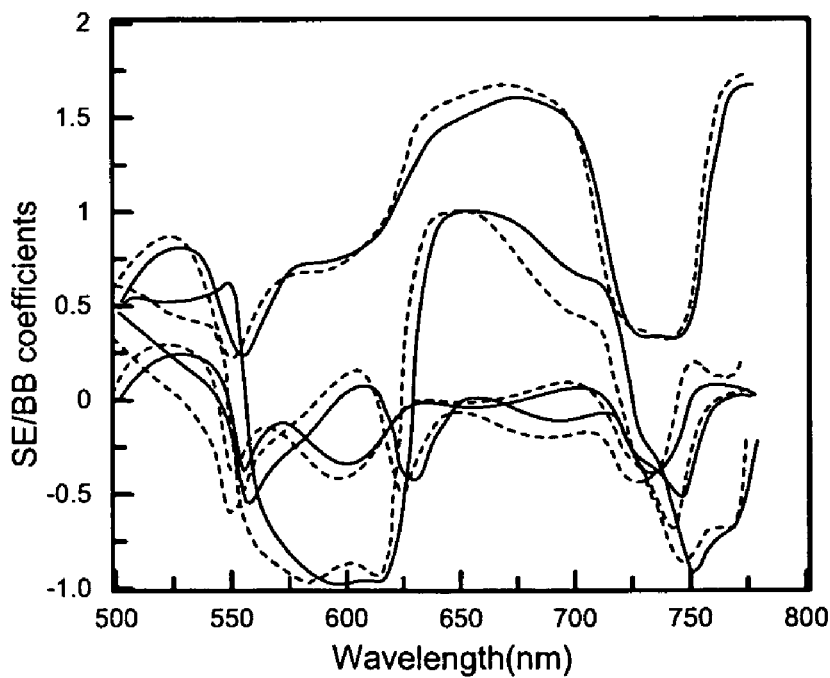
Figure 16F:
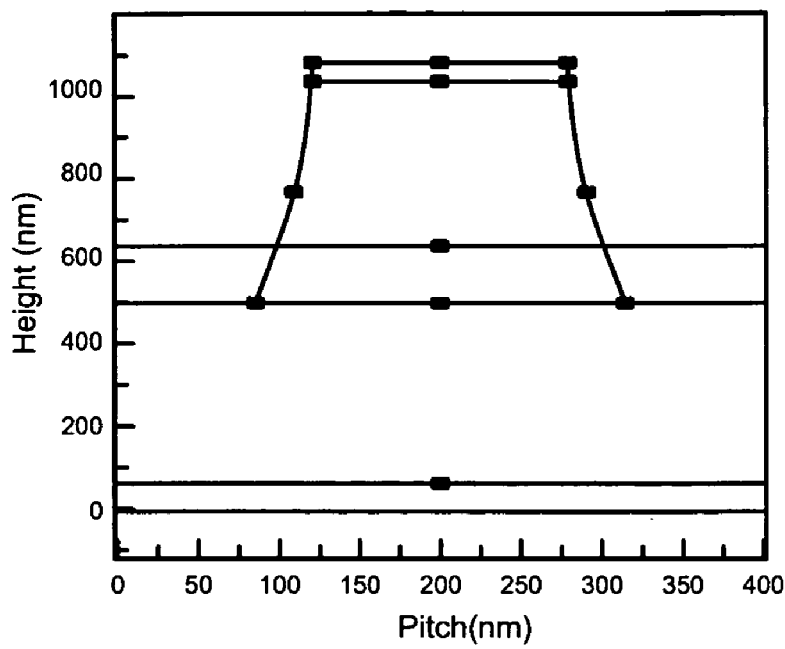
Figure 16G:
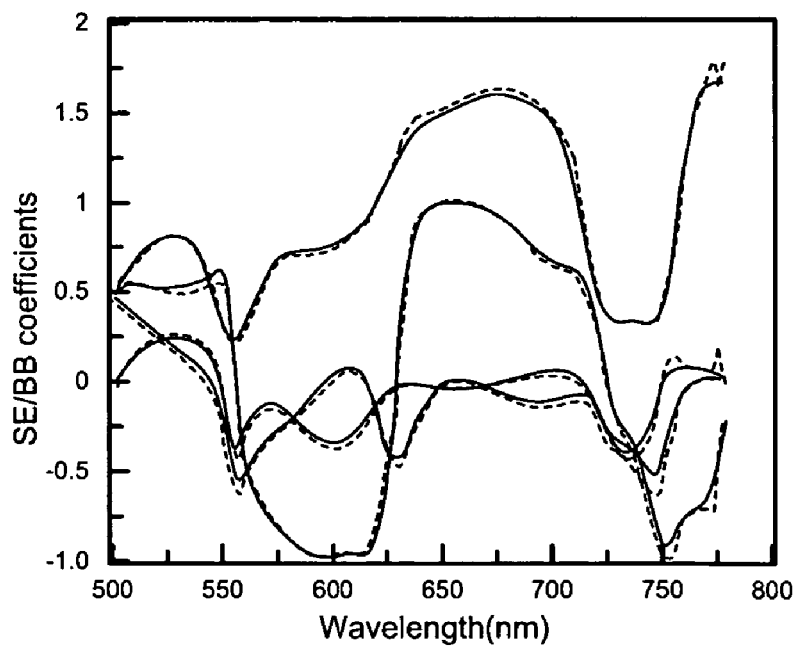

Spectral fitting component 602 provides the user with visual feedback to guide the design process. As an example, FIG. 16A shows a five layer sample displayed in the gross model definition of shows film structure component 604. FIG. 16B shows the corresponding model displayed in interactive shape modeling component 610. Activating the "Calc Once" button of film structure component 604 produces the spectra shown in spectral fitting component 602 of FIG. 16C. At this point, the user can choose to interactively alter the model displayed in interactive shape modeling component 610 or take other steps to improve the goodness of fit. FIG. 16D shows the case where the user has added an additional control point (using layer property component 606) and interactively moved the new control point using (in interactive shape modeling component 610) to change the line profile of the sample being modeled. Hitting the "Calc Once" button a second time produces the spectra shown in spectral fitting component 602 of FIG. 16E. By inspection, it is clear that there is now a much greater correspondence between expected and calculated spectra. This means that the change in line profile shape was beneficial. FIGS. 16F and 16G show the result of the user activating the "Calc & Fit" button of film structure component 604. This has caused additional changes in the shape of the line profile being modeled and increased the goodness of fit between expected and calculated spectra.

Figure 17:
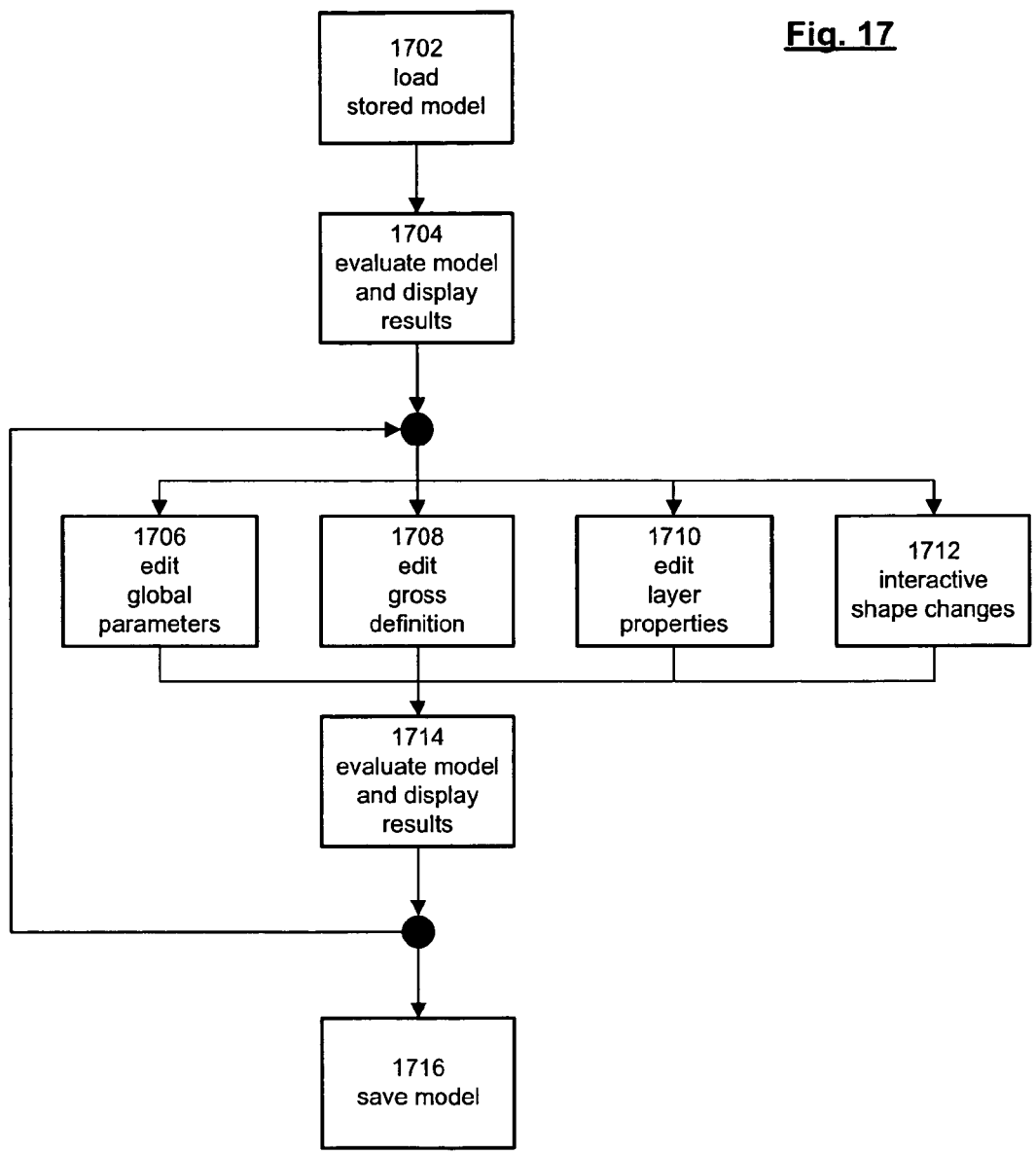

In general, it is not possible to specify an exact sequence of steps used during a typical use of the interactive environment. However, as shown in FIG. 17, a user might begin such as session by loading an existing model typically located on disk or another secondary storage device. The existing model may be the end result of a previous use of the interactive environment, or may have been created in some other fashion, including manual specification. Loading the model causes all of the components of the visual design environment to be updated. In particular, this means that the loaded model is shown, both in the gross model definition of film structure component 604, as well as in interactive shape modeling component 610.

Once loaded, the user will typically use the interactive environment to evaluate the model using the "Calc Once" or "Calc & Fit" buttons (represented by step 1704). This causes the calculated spectral response information to be displayed along with the corresponding empirical response information in spectral fitting component 602. At this point, the user has a clear picture of how closely the model matches the corresponding empirical results. Typically, the user would then modify the model in some way. As represented by step 1706, this could include changes to global parameters through the use of the global parameters component 608. Alternately, film structure component 604 may be used to alter the gross definition of the model (represented by step 1708). This could include, for example, adding or deleting layers, spacers or trench fills. Changes may also be made to individual layers using layer property component 606 (shown as step 1710). More intuitive are change made using interactive shape modeling component 610 (as shown in step 1712). To make these changes, the user drags control points within the representation of the model in interactive shape modeling component 610. As the user makes these interactive changes, it is typically to use layer property component 606 to add or delete control points.

Once the user has made one or more model changes, it is typical to reevaluate the model using the "Calc Once" or "Calc & Fit" buttons (represented by step 1714). Once again, the corresponding results are displayed along with the corresponding empirical response information in spectral fitting component 602. After the re-evaluation, the user can decide if the new calculated results are sufficiently close to the empirical data. Typically, the process of model modification followed by re-evaluation will be repeated for at least several iterations. In each case, the user is able to determine if each incremental change is beneficial or harmful. This allows the user to proceed in an almost trial and error fashion where a series of educated guesses are used to refine the model until acceptable results are obtained. At that point, a typical use of the interactive environments ends with the user saving the modified model (see 1716).

What is claimed is:

1. An interactive design interface for creating a theoretical model of a semiconductor sample having one or more geometrical features formed thereon, said interface comprising:
   a first display region for inputting information defining one or more parameters of the sample selected from the group consisting of number of layers, layer thickness, and material composition; and
   a second display region for displaying a representation of a model of the sample based on the information input into the first display region, said model further including control points defining the shape of the geometrical feature, said second display region permitting the user to modify the position of the control points to vary the shape of the feature.

2. An interface as recited in claim 1, further including a third display region for displaying theoretical optical response data, said data being calculated based on the information contained about the sample in the first and second display regions.

3. An interface as recited in claim 2, wherein said optical response data is recalculated and displayed in the third display region in response to changes of information entered into either the first or second display regions.

4. An interface as recited in claim 2, wherein said third display region also includes actual optical response data derived from measuring a physical sample in a manner to allow comparison between the theoretical data and the actual data.

5. An interface as recited in claim 4, further including a processor for performing a regression based analysis between the actual data and the theoretical data by changing the shape and/or parameters of the model so that the calculated data more closely matches the actual data and updating at least one of the first and second display regions with the changed shape or parameters.

6. An interactive design interface for creating a theoretical model of a multi-layer semiconductor sample having one or more geometrical features formed thereon, said feature having at least one height and width, said interface comprising:
   a first display region for inputting information defining parameters of the sample, said parameters including the number of layers, layer thickness, material composition of the layers and the height and width of the geometrical feature;
   a second display region for displaying a representation of a model of the sample based on the information input into the first display region, said model further including at least one control point corresponding to the height of the feature and at least one control point corresponding to the width of the feature, said second display region permitting the user to modify the position of the control points to vary the shape of the feature; and a third display region for displaying theoretical optical response data, said data being calculated based on the information contained about the sample in the first and second display regions.

7. An interface as recited in claim 6, wherein said optical response data is recalculated and displayed in the third display region in response to changes of information entered into either the first or second display regions.

8. An interface as recited in claim 6, wherein said third display region also includes actual optical response data derived from measuring a physical sample in a manner to allow comparison between the theoretical data and the actual data.

9. An interface as recited in claim 8, further including a processor for performing a regression based analysis between the actual data and the theoretical data by changing the shape and/or parameters of the model so that the calculated data more closely matches the actual data and updating at least one of the first and second display regions with the changed shape or parameters.

10. An interface as recited in claim 6, wherein at least some of the control points correspond to layer boundaries.

11. An interface as recited in claim 6, wherein at least some of the control points do not correspond to layer boundaries and define a global shape of representation of the feature in the model.

12. A method of creating a theoretical model of a semiconductor sample having one or more geometrical features formed thereon:
   (a) displaying an initial representation of the model, said model including layers and at least one geometrical feature having at least one height and width, said representation including at least one control point corresponding to the height and at least one control point corresponding to the width;
   (b) adjusting the model by one or more of:
      (i) adding control points to specify more complex shapes;
      (ii) adding control points to reflect additional features; or
      (iii) moving control points to change the shape of the feature; and
   (c) storing the adjusted model in a database.

13. A method as recited in claim 12, further including the step of displaying theoretical optical response data, said data being calculated based on the characteristics of the model.

14. A method as recited in claim 13, further including displaying actual optical response data derived from measuring a physical sample along with the theoretical response data.

15. A method as recited in claim 14, wherein the step of adjusting the model is performed one or more times in order to reduce the differences between the theoretical data and the actual data.

16. A method as recited in claim 12, wherein at least some of the control points correspond to layer boundaries.

17. A method as recited in claim 12, wherein at least some of the control points do not correspond to layer boundaries and define a global shape of representation of the feature in the model.

18. A method as recited in claim 17, wherein the control points are added and/or moved to reflect local distortions of the representation of the model.

19. A method as recited in claim 17, wherein a spline function is used to calculate the curvature of the edge of the representation of the feature in the model.

* * * * *

UNITED STATES PATENT AND TRADEMARK OFFICE
CERTIFICATE OF CORRECTION

| | | |
|---|---|---|
| PATENT NO. | : 7,613,598 B2 | Page 1 of 1 |
| APPLICATION NO. | : 11/542806 | |
| DATED | : November 3, 2009 | |
| INVENTOR(S) | : Opsal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 654 days.

Signed and Sealed this

Nineteenth Day of October, 2010

David J. Kappos
*Director of the United States Patent and Trademark Office*